United States Patent [19]

Della Valle et al.

[11] Patent Number: 5,550,249
[45] Date of Patent: Aug. 27, 1996

[54] WATER SOLUBLE DERIVATIVES OF BIOTIN AND RELATED THERAPEUTICAL COMPOSITIONS

[75] Inventors: Francesco Della Valle; Silvana Lorenzi, both of Padova; Gabriella Calderini, Carrara San Giorgio, all of Italy

[73] Assignee: Lifegroup, S.p.A., Rome, Italy

[21] Appl. No.: 200,545

[22] Filed: Feb. 22, 1994

Related U.S. Application Data

[63] Continuation of Ser. No. 986,390, Dec. 7, 1992, abandoned.

[30] Foreign Application Priority Data

Dec. 31, 1991 [IT] Italy .................. MI91A3507

[51] Int. Cl.$^6$ .................. C07D 495/04; A61K 31/38
[52] U.S. Cl. .................. 548/303.7
[58] Field of Search .................. 548/303.7; 514/387

[56] References Cited

U.S. PATENT DOCUMENTS

| | | | |
|---|---|---|---|
| 2,502,422 | 4/1950 | Cheney | 548/303.7 |
| 3,290,324 | 12/1966 | Lubowe | 548/303.7 |
| 3,658,837 | 4/1972 | Hanka et al. | 548/303.7 |
| 4,584,191 | 4/1986 | Hostettler et al. | 548/303.7 |
| 5,162,344 | 11/1992 | Koch | 514/356 |
| 5,166,168 | 11/1992 | Stiefel | 514/387 |

OTHER PUBLICATIONS

Mar., Advanced Organic Chemistry, 1985, pp. 371–372.
Chemical Abstract, Abstract No. 103201 (JP–A–02 096 581), vol. 113, No. 12, Sep. 1990, p. 382.
Chemical Abstract, Abstract No. 220096k (JP–A–04 169 528), vol. 117, No. 22, Nov. 30, 1992, p. 526.
"Tetrahydropyridyloxadizoles: Semirigid Muscarinic Ligands," J. Med. Chem. 1991, 34, pp. 1086–1094, Graham A. Showell et al.
"Synthesis and Muscarinic Activities of Quinuclidin–3–yltriazole and –tetrazole Derivatives," J. Med. Chem. 1992, 35, pp. 1280–1290, Harry J. Wadsworth et al.
"Novel Functional $M_1$ Selective Muscarinic Agonists. Synthesis and Structure–Activity Relationships of 3–(1,2, 5–Thiadiazolyl)–1,2,5,6–tetrahydro–1–methylpyridines," J. Med. Chem. 1992, 35, pp. 2274–2283, Per Sauerberg et al.
"Muscarinic Cholinergic Binding in Rat Brain," Proc. Nat. Acad. Sci. USA, vol. 71, No. 5, pp. 1725–1729, May 1974, Henry I. Yamamura et al.
"Multiple in Vitro Interactions with and Differential in Vivo Regulation of Muscarinic Receptor Subtypes by Tetrahydroaminoacridine," The Journal of Pharmacology and Experimental Therapeutics, vol. 250, No. 2, pp. 573–581, Donna D. Flynn et al. (1989).

Primary Examiner—David B. Springer
Attorney, Agent, or Firm—Watson Cole Stevens Davis, P.L.L.C.

[57] ABSTRACT

Salts of biotin are described with alkanolamines and the respective water soluble therapeutical compositions, suitable to be orally, parenterally and topically administered.

The compositions above are particularly suitable for the treatment of the vitamin H deficiency, having a dermatologic manifestation, for the treatment of the insufficiency in multiple carboxylase enzymes, for the treatment of dermatologic phatologies, like the seborrheal dermatitis in the newborn, and for the treatment of diabetic neuropathies.

8 Claims, No Drawings

WATER SOLUBLE DERIVATIVES OF BIOTIN AND RELATED THERAPEUTICAL COMPOSITIONS

This application is a Continuation of application Ser. No. 07/986,390, filed Dec. 7, 1992, now abandoned.

BACKGROUND OF THE INVENTION

1) Field of the Invention

The present invention relates to water soluble salts of biotin and to the relative therapeutical compositions, which can be administered by oral, parenteral and topical route, particularly suitable for the treatment of vitamin H deficiency, with dermatological manifestation, for the treatment of the deficiency in multiple carboxylase enzymes in the different phases of childhood, for the treatment of dermatologic pathologies, like the seborrheal dermatitis of the newborn, and for the treatment of diabetes and its complicating diseases.

2) The State of the Art

The clinical role of biotin, better known as vitamin H and characterized by the following formula:

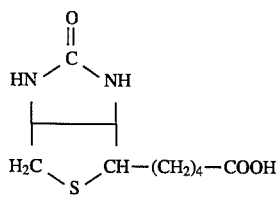

was ascertained in 1942 by Sidenstricker and co-workers, who demostrated that the socalled "egg-white injury" can be defeated administering biotin.

The experimental work hereinabove aimed to show which were the effects of a vitamin H deficiency in human beings. In fact the patients undergoing such a treatment were only fed with egg-white, wherein biotin combines with a protein, the avidin, which prevents its bioavailability, thus causing a state of deficiency. This experimental work and the successive ones clearly proved that such vitamin deficiency in human beings leads to the formation of a non-pruriginous dermatitis and then to maculosquamosal dermatitis, change of the mental state, myalgia, hyperesthesis, localized paresthesis, anorexia, coronary ischemia.

All these secondary effects disappeared and the patients came back to normality following administration of biotin for a certain time. Moreover, in the last 20 years the interest was aroused in the application of the therapeutical use of molecules effective as cofactors in several enzymatic reactions. It was thus proved that biotin can be a therapeutical cofactor like pyridoxine or vitamin D. It was for instance proved that although biotin is uneffective in treating diseases caused by single carboxylase enzymes insufficiency, like the insufficiency in propionyl-Co A carboxylase (being the cause of ketonic hyperglycinemia), the insufficiency in pyruvate-carboxylase (being the cause of lactic acidosis, persistent in the different phases of childhood), and the insufficiency in β-methyl-crotonylcarboxylase (which can also cause juvenile spinal muscular atrophy, or, always during the childhood, a serious acidosis bound to metabolic disorders), the same biotin proved on the contrary to be effective in diseases coming from a deficiency in multiple carboxylase enzymes, whose symptoms are mostly common to those of the pathologies hereinabove, and provoked by deficiencies in single carboxylase enzymes (K. S. ROTH "Biotin in clinical medicine—a review "The American Journal of clinical nutrition" 34: September 1981, pp. 1967–1974).

Vitamin H also proved to be particularly effective in the treatment of the seborrheal dermatitis in the newborn, whose origin was not yet ascertained; probably such dermatitis seems to be abscribed to the low amount of vitamin H in the breast milk and possibly to poor digestion or persistent diarrhoeia (Khrishnamurti-Dachshinamurti and Jasbir Chauan-Biotin-Vitamins and Hormones, vol 45–1989 PP 337–385).

Biotin moreover can advantageously be utilized in the therapy of diabetes and its complicating diseases.

It has recently been proved through pharmacological tests on mice as well as through clinical tests on human beings that said active principle not only lowers the blood glucose level in insulin-dependent diabetics, but can also reduce the post-prandial glucose level, increase glucose tolerance and lower resistance to insulin also in insulin-independent diabetes (Alluru Reddi, Barbara De Angelis, Oscar Frank, Norman Lasker and Herman Baker "Biotin supplementation improves glucose and insulin tolerances in genetically diabetic KK mice" Life Science, Vol. 42, pp 1323–1330; Coggeshall, J. C. et al Ann N.Y. Acad. Science 447–1985 pp. 389–392). Furthermore, it has also recently been proved that such active principle can be advantageously utilized in human beings for the treatment and the prevention of a typical diabetes complicating disease, namely peripheral neuropathies having diabetic origin (D. Koutsikos, B. Agroyannis, H. Tsanakos-Exarchou "Biotin for diabetic peripheral neuropathy; Biomed & Pharmacother (1990) 44, 511–514). Recent studies have shown that biotin is able to activate the enzyme glucokinase as well as insulin.

It is known in fact that the enzyme glucokinase controls the haematic glucose, namely glycaemia, by contemporaneously controlling the utilization and the storage of hepatic glucose, in the form of glycogen, and it is believed that in the pancreas islets the glucokinase acts as a sensor for the glucose controlling the insulin production (J. Chauan, K. Dackshinamurti, J. Biol. Chem:, 266, 1991; pages 10035–38).

Notwithstanding such remarkable therapeutical potential, the uses of biotin are drastically limited because of its poor water solubility. In order to overcome these drawbacks, biotin is employed, according to EP 036902, in the presence of cyclodextrins and of low amounts of a 28% ammonia (solution). These compositions, before being used, are in any case spray dried.

U.S. Pat. No. 4,277,488 describes compositions similar to those of the preceding patent the sole difference residing in that lactose is used instead of cyclodextrin.

Both the compositions above in any case encopass an oral administration of vitamin H.

U.S. Pat. No. 4,725,427 describes water soluble effervescent compositions of vitamins and among them of biotin. In this case the solubility of such active principle is enhanced either by the presence of lactose of by the presence of metals like Ca, Mg, Cu, Zn, Fe and/of Mn, in the form of an amino acid chelate.

According to this patent, therefore, it is still necessary, in order to reach a greater solubilization of biotin, the presence of lactose, coupled with particular metallorganic derivatives. Moreover also in this patent, like, on the other hand, in the other papers hereinabove, the sole administration route encompassed for biotin, is the oral one.

Because of the impossibility to obtain in a simple way the solubilization of biotin without using said complicated methods, the biotin administration by a route different from the oral one was never taken into serious consideration.

Only according to JP Pat. Appln. 2096581 as summarized in Derwent Data Bank biotin previously converted into an ester is topically administered on the skin or on hair utilizing as the vehicle a gel or creamy suspension of water and of an organic solvent.

These biotin esters, partially soluble either in the organic solvent of in water, proved to be particularly fit for this goal.

The need was felt for biotin derivatives allowing the use of such active principle not only by oral route but also by parenteral and in particular by intramuscular or intravenous route.

DISCLOSURE OF THE INVENTION

The Applicant has now unexpectedly found some derivatives of biotin which are completely water soluble and can therefore be advantageously administered by oral, parenteral or topical route. The present invention relates to the salts of biotin with an aminoalcohol and, in particular, to those salts which are generally defined as biotinate of alkanolammonium. The Applicant has in fact unexpectedly found out that said salts are completely soluble in water and therefore much more soluble than biotin as such, showing only a solubility of 22 mg/100 ml.

The present invention further relates to a process for preparing said salts, comprising the following steps:

a) adding to the suspension of biotin in an alcoholic solvent alkanolamine in amounts exceeding 10% the stoichiometric one;

b) cooling to 0° C. the solution obtained in step a) and precipitating the salt obtained by addition of a ketonic solvent, previously cooled to a temperature lower than 5° C.;

c) recovering the salt obtained in step (b).

The present invention further relates to pharmaceutical compositions, containing, as the active principle, at least one of the biotin salts of amino alcohols (biotinates), in combination with suitable excipients and/or diluents.

DETAILED DESCRIPTION OF THE PRESENT INVENTION

The salts of biotin object of the present invention are preferably the biotinate of ethanolammonium, characterized by the following formula:

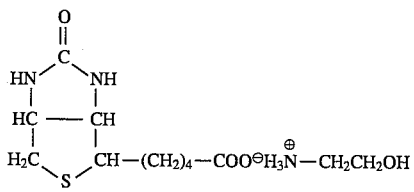

the biotinate of diethanolammonium, characterized by the following formula:

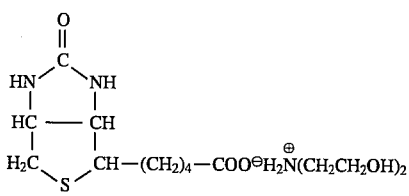

and the biotinate of triethanolammonium, characterized by the following formula:

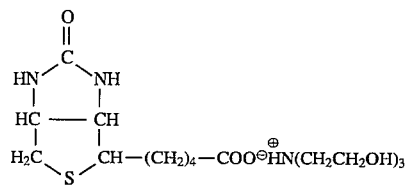

The solvent of step (a) of the process according to the present invention is preferably methanol, whereas the ketonic solvent, utilized in step (b), to precipitate the salt, is preferably acetone, previously cooled to a temperature from 1° to 3° C.

The salt is preferably recovered by filtration and dried on $P_2O_5$ or on NaOH pellets.

The pharmaceutical compositions according to the present invention are therefore suitable either for the oral or for the parenteral administration, preferred parenteral administration are those occurring by rectal, intramuscular or intravenous route.

The therapeutical compositions according to the present invention may be in particular advantageously used for the treatment of the insufficiency in multiple carboxylase enzymes in the various phases of the childhood for the treatment of the dermatologic pathologies, like the seborrheal dermatitis of the newborn, as well as for the treatment of diabetes and of diabetes neuropathies.

The following examples are supplied for illustrative purposes but do not limit in any way the present invention.

EXAMPLE 1

(Preparation of ethanolamine biotinate)

7.32 g of biotin (d-Biotin, from Hoffman La Roche) (0.03 mol) are suspended in 30 ml methanol. A slight excess of ethanolamine (0.04 mol) is added to the suspension and the solution obtained becomes immediately clear. 100 ml of cold acetone (1°–3° C.) are added to this clear solution thereby obtaining the precipitation of the crystals of the salt. After 1 h at 0° C. the precipitate is filtered and dried for 12 h on $P_2O_5$ or on NaOH pellets. Before carrying out the filtration of the precipitate, should an excess of alcohol or of ethanolamine have been used in the reaction, it is better to reduce the volume of the mixture containing the precipitate, however avoiding that the evaporation lasts longer than 30–60 minutes, because ethanolamine, under such conditions, exhibits rather a high vapor pressure.

8.42 g of ethanolamine biotinate are thus obtained showing the following features:

Melting point: 223° C. (biotin has a m.p.=232° C.). The salt is completely water soluble and rather soluble in cold ethanol.

UV ANALYSIS

The analysis, performed by means of an UV spectrophotometer, showed that the cation had a slight "blueshift" ($\lambda_{max}$ shifts from 210.3 to 209.7 nm) and a slight hyperchromic effect ($\lambda_{mol}$ shifts from 7.027 to 7.118).

ELEMENTAL ANALYSIS

Raw formula of ethanolamine biotinate: $C_{12}H_{23}N_3O_4S$ (molecular weight: 305.39).

|  | C | H | N | S | O* |
|---|---|---|---|---|---|
| calculated (%) | 47.15 | 7.53 | 13.75 | 10.47 | 20.95 |
| found (%) | 46.81 | 7.65 | 13.78 | 10.98 | 21.02 |

(*) value obtained by difference

NMR ANALYSIS

The product was analyzed by NMR spectrography by using an apparatus BRUKER MOD. WP 200 SY and by using as a blank tetramethylsilane. On the basis of such analysis it was possible to see that the analyzed product showed the typical peaks of biotin and also the typical signals of ethanolamine.

IR ANALYSIS

The IR analysis was performed by means of a Perkin Elmar apparatus using solid KBr. The comparison between biotin and ethanolamine biotinate shows, in the latter, additional bands respectively corresponding to the following bands: 1028; 1085; 1312; 1471; 1550 and 2911 $cm^{-1}$. The last two bands can be attributed to the stretching of the groups —OH and —$NH_3^+$.

Partition in water/octanol.

$^{14}$C-biotin (53000 dpm) was used admixed with cool biotin (0.25 mmol) in 5 ml of twice distilled water, in the presence and in the absence of ethanolamine (3 µl), then adding 5 ml of octanol and stirring (1 minute by means of a stirrer VORTEX). After separation of the phases the radioactivity was measured by scintillation (Beckman counter) in 1 ml of sample. The amount of $^{14}$C-biotin transferred into the octanolic phase was 14443 dpm in the absence of ethanolamine and 82 dpm in the presence of ethanolamine.

This confirms the increase in solubility in the aqueous phase, which is a consequence of the salification. Should the aqueous phase be brought up to pH 4, the amount of $^{14}$C-biotin transferred into the octanolic phase always remains the same, in the absence of ethanolamine, while increasing 170 times in the presence of ethanolamine (see table 1).

This effect depends on the decreased dissociation of the —COOH group and on the protonation of the —$NH_2$ group.

TABLE 1

| partition in water/octanol (average of 3 tests). | | | |
|---|---|---|---|
|  | $H_2O$ (dpm) | octanol | $H_2O$/octanol |
| Biotin | 40940 | 14443 | 2.8 |
| Ethanolamine biotinate | 36664 | 82 | 447.1 |
| Biotin at pH 4 | 40769 | 13991 | 2.9 |
| Ethanolamine biotinate at pH 4 | 32148 | 12300 | 2.6 |

EXAMPLE 2

Preparation of diethanolamine biotinate

Diethanolamine biotinate was prepared, according to the same methodology described in Example 1, by reacting biotin with diethanolamine.

EXAMPLE 3

Preparation of triethanolamine biotinate

Triethanolamine biotinate was prepared, according to the same methodology described in Example 1, by reacting biotin with triethanolamine.

PHARMACEUTICAL COMPOSITIONS

A water soluble tablet weighing 100 mg contains:

| Monoethanolamine biotinate | 6.2 mg |
|---|---|
| Glycocoll | 61.8 mg |
| Sodium Carboxymethylstarch | 25.0 mg |
| Polyethylene glycol 6000 | 4.2 mg |
| Cornstarch | 1.0 mg |
| Polyvinylpyrrolidone | 0.3 mg |
| Peach aroma | 1.5 mg |

A 1 g sachet of granular product contains:

| Monoethanolamine biotinate | 6.2 mg |
|---|---|
| Glycocoll | 963.8 mg |
| Polyvinylpyrrolidone | 5 mg |
| Polyethylene glycol 6000 | 5 mg |
| Peach aroma | 20 mg |

A 2 ml injectable vial contains:

| Monoethanolamine biotinate | 6.2 mg |
|---|---|
| Sodium phosphate, dibasic 12$H_2O$ | 6 mg |
| Sodium phosphate, monobasic | 0.5 mg |
| Sodium chloride | 12 mg |
| Water for injectable preparations q.s. to | 2 ml |

A 10 g gel tube contains:

| Monoethanolamine biotinate | 62 mg |
|---|---|
| Ethanol | 1.5 g |
| Carboxypolymethylene (Carbopol) | 200 mg |
| Meglumine | 300 mg |
| Sodium edetate (tetrasodium EDTA) | 1 mg |
| Neroli oil | 0.15 ml |
| Deionized water q.s. to | 10 g |

Similar compositions were prepared by using diethanolamine biotinate sad triethanolamine biotinate.

We claim:

1. A biotinate of an alkanolammonium of the formula:

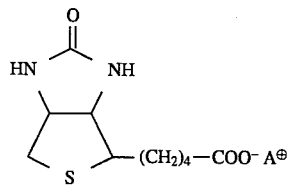

wherein $A^{\oplus}$ is selected from the group consisting of: $H_3N^{\oplus}CH_2CH_2OH$, $H_2N^{\oplus}(CH_2CH_2OH)_2$ and $HN^{\oplus}(CH_2CH_2OH)_3$.

2. A method for treating multiple carboxylase enzyme insufficiency in humans comprising orally, parenterally or topically administering a pharmaceutically effective amount of a compound of the formula of claim 1.

3. A pharmaceutical composition containing as the active ingredient a therapeutically effective amount of a compound of the formula of claim 1 in combination with suitable excipients and/or diluents.

4. The method according to claim 2 for the treatment of seborrheal dermatitis in the newborn.

5. The method according to claim 2 for the treatment of diabetes and diabetic neuropathies.

6. The pharmaceutical composition according to claim 3, in the form of solutions suitable for parenteral administration.

7. The pharmaceutical composition according to claim 3, in the form of gels or solutions suitable for topical administration.

8. The pharmaceutical composition according to claim 3, in the form of sachets or tablets suitable for oral administrations.

* * * * *